US009500525B2

(12) United States Patent
Teraoka et al.

(10) Patent No.: US 9,500,525 B2
(45) Date of Patent: Nov. 22, 2016

(54) MULTI-ANGLE COLORIMETER

(75) Inventors: Yoshitaka Teraoka, Osaka (JP);
Katsutoshi Tsurutani, Osaka (JP);
Yuta Yamanoi, Toyonaka (JP)

(73) Assignee: Konica Minolta, Inc., Tokyo (JP)

( * ) Notice: Subject to any disclaimer, the term of this patent is extended or adjusted under 35 U.S.C. 154(b) by 164 days.

(21) Appl. No.: 14/114,117

(22) PCT Filed: Apr. 9, 2012

(86) PCT No.: PCT/JP2012/059666
§ 371 (c)(1),
(2), (4) Date: Oct. 25, 2013

(87) PCT Pub. No.: WO2012/147504
PCT Pub. Date: Nov. 1, 2012

(65) Prior Publication Data
US 2014/0049776 A1    Feb. 20, 2014

(30) Foreign Application Priority Data
Apr. 28, 2011   (JP) ................................. 2011-101740

(51) Int. Cl.
*G01J 3/50*     (2006.01)
*G01N 21/25*    (2006.01)
(Continued)

(52) U.S. Cl.
CPC ............... *G01J 3/50* (2013.01); *G01J 3/502* (2013.01); *G01J 3/504* (2013.01); *G01N 21/251* (2013.01);
(Continued)

(58) Field of Classification Search
CPC ......... G01J 3/504; G01J 3/50; G01N 2021/4711; G01N 21/251; G01N 2021/575; G01N 21/57
See application file for complete search history.

(56) References Cited

U.S. PATENT DOCUMENTS 5,592,294 A     1/1997  Ota et al.
6,707,553 B1 *  3/2004  Imura ...................... G01J 3/10
                                                  356/402
(Continued)

FOREIGN PATENT DOCUMENTS

JP   5-273042   10/1993
JP   10-137194   5/1998
(Continued)

OTHER PUBLICATIONS

Search Report dated Aug. 25, 2014 issued in the corresponding European Patent Application No. 12 77 6651.7.
(Continued)

*Primary Examiner* — Kara E Geisel
*Assistant Examiner* — Shawn Decenzo
(74) *Attorney, Agent, or Firm* — Cozen O'Connor

(57) ABSTRACT

In a multi-angle colorimeter, a light detecting portion 40 includes a main light receiving window disposed in a predetermined position on a main geometry plane, and first and second auxiliary light receiving windows disposed on a secondary geometry plane, and a main photoelectric conversion element for converting a main component light received by the main light receiving window in a light reflected from a measurement point into an electrical main signal and first and second auxiliary photoelectric conversion elements for converting first and second auxiliary component lights received by the first and second auxiliary light receiving windows in the reflected light respectively into first and second electrical auxiliary signals. A calculating portion corrects the electrical main signal based on the first and second electrical auxiliary signals to obtain color information about the measurement point.

5 Claims, 15 Drawing Sheets

(51) Int. Cl.
*G01N 21/57* (2006.01)
*G01N 21/47* (2006.01)

(52) U.S. Cl.
CPC ..... *G01N 21/255* (2013.01); *G01N 2021/4711* (2013.01); *G01N 2021/4735* (2013.01); *G01N 2021/575* (2013.01); *G01N 2201/0221* (2013.01)

(56) References Cited

U.S. PATENT DOCUMENTS

| | | |
|---|---|---|
| 7,027,160 B2 | 4/2006 | Sperling |
| 2002/0118357 A1* | 8/2002 | Torfs et al. ............ 356/128 |
| 2005/0286053 A1 | 12/2005 | Imura |

FOREIGN PATENT DOCUMENTS

| | | |
|---|---|---|
| JP | 2002-005830 | 1/2002 |
| JP | 2006-010508 | 1/2006 |
| JP | 2007-170858 | 7/2007 |

OTHER PUBLICATIONS

Office Action dated Sep. 2, 2014 issued in the corresponding Japanese Patent Application No. 2013-511994.

\* cited by examiner

| POSTURE ERROR θ | OUTPUT RATIO R | CORRECTION FACTOR C |
|---|---|---|
| θ1 | R1 | C1 |
| θ2 | R2 | C2 |
| θ3 | R3 | C3 |
| ... | ... | ... |

FIG. 11

F I G. 1 5
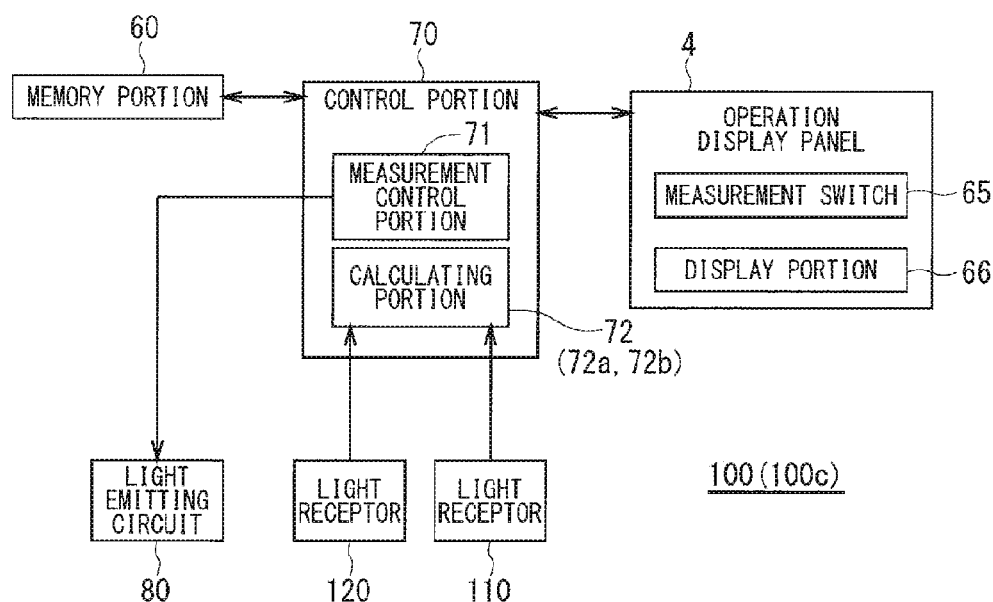

MULTI-ANGLE COLORIMETER

RELATED APPLICATIONS

This application is a U.S. National Phase Application under 35 USC 371 of International Application PCT/JP2012/059666 filed Apr. 9, 2012.

This application claims the priority of Japanese application No. 2011-101740 filed Apr. 28, 2011, the entire content of which are hereby incorporated by reference.

TECHNICAL FIELD

The present invention relates to a multi-angle colorimeter and more particularly to a technique for improving an optical configuration for correcting a posture error of a colorimeter with respect to a measurement plane.

BACKGROUND ART

In some cases, a color of metallic painting, pearl color painting and the like to be used in painting for a car and the like is seen to be different depending on a direction of an observer under the influence of a brilliant material in an inner part. For this reason, a multi-angle colorimeter for carrying out illumination or light reception at a plurality of angles is used for evaluation of the painting (evaluation of a paint color).

In other words, the metallic painting and the pearl color painting which is to be used in painting for a car and the like is constituted by containing, in a painted film, a flaky aluminum piece and mica piece which is referred to as a brilliant material and produces a so-called metallic effect and pearl effect. This is caused by the fact that contribution of the brilliant material to a reflection characteristic is varied depending on illuminating and observing directions. A multi-angle colorimeter having a multi-angle geometry (an optical configuration) is used for evaluating the metallic painting and pearl color painting (colorimetry). The multi-angle colorimeter serves to carry out illumination over a measurement plane of an object to be measured in a plurality of directions to perform light reception in one direction (multi-direction illumination and one direction light reception) or to carry out the illumination over the measurement plane of the object to be measured in one direction to perform the light reception in a plurality of directions (one direction illumination and multi-direction light reception).

If a measuring target is a sample having a curvature, for example, a bumper of a car or the like, however, there is a high possibility that a posture error in which a sample normal and a reference axis of a colorimeter are not coincident with each other in measurement might be made. Above all, an angular direction which is close to a regular reflected light has a great angular dependency of a reflection characteristic. For this reason, the influence of the error cannot be ignored.

In order to reduce the posture error, therefore, there is proposed the technique in which an optical base unit including a measuring optical system is held by an elastic body such as a spring with respect to a housing and an illumination and light reception geometry is maintained to be constant without depending on a contact angle of a sample and the housing to reduce the measurement error by the method disclosed in Japanese Patent Application Laid-Open No. 2002-5830,for example.

As another well-known technique, moreover, there is also the technique for suppressing the posture error of the colorimeter by employing the structure in which a plurality of contact pins are disposed on a sample contact surface and measurement trigger is applied if all of them are pressed uniformly.

PRIOR ART DOCUMENT

Patent Document

SUMMARY OF THE INVENTION

Problems to be Solved by the Invention

Although typical use of the multi-angle colorimeter includes evaluation of an exterior of a car, it can easily be imagined that the colorimeter is inclined when used in the case in which it is used in a manufacturing line or the like, particularly, the case in which a side surface of a body of the car such as a bumper is measured.

In the technique of Japanese Patent Application Laid-Open No. 2002-5830, however, a contrivance is applied to a mechanism in order to reduce a posture error. However, it is necessary to employ a complicated mechanical construction in respect of a structure in which an internal mechanism is held by an elastic body. Consequently, a device is made large-sized. Because of the structure in which the internal mechanism is moved, moreover, there is a fear that reliability or durability might be poor in the case of use on a strict condition, for example, the case in which a measuring target is moved in a manufacturing line for a car or the like.

Moreover, the well-known technique has a drawback that a measurer needs to manually adjust a posture and a labor and time is required for starting measurement.

In consideration of the circumstances, it is an object of the present invention to provide a multi-angle colorimeter capable of maintaining reliability and durability of an internal mechanism and correcting a posture error without requiring a labor and time also in the case in which the colorimeter is inclined and thus used with respect to a measurement plane.

Means for Solving the Problems

A multi-angle colorimeter according to an aspect of the present invention includes: (a) an illuminating portion disposed on a virtual reference plane including a predetermined reference line and carrying out light irradiation toward a predetermined measurement point defined on the reference line; (b) a light detecting portion; the light detecting portion including: a main light receiving window disposed in a predetermined position on the reference plane; a plurality of auxiliary light receiving windows disposed on a plane which has the predetermined position and the predetermined measurement point and is orthogonal to the reference plane, and opposed to the measurement point respectively; a main photoelectric conversion element for receiving a main component light received by the main light receiving window in a reflected light from a measurement plane disposed on the measurement point and converting the main component light into an electrical main signal; and a plurality of auxiliary photoelectric conversion elements for receiving a plurality of auxiliary component lights received by the plurality of auxiliary light receiving windows in the reflected light and converting the plurality of auxiliary component lights into a plurality of electrical auxiliary signals, and (c) a calculating portion for correcting the electrical main signal based on the plurality of electrical auxiliary signals, thereby obtaining color information about the measurement plane which is present on the measurement point.

Effects of the Invention

According to the structure, the electrical main signal is corrected based on the information about the light component obtained from the plurality of auxiliary light receiving windows disposed on the plane which includes the predetermined position and the measurement point and is orthogonal to the reference plane. Therefore, it is possible to appropriately carry out colorimetry even if the reference plane is inclined from the normal of the measurement plane.

BRIEF DESCRIPTION OF DRAWINGS

FIG. 11 is a diagram illustrating a table for a posture error θ, an output ratio R and a correction factor C.

FIG. 15 is a diagram showing an example of a basic functional configuration of the multi-angle colorimeter for receiving lights reflected at different angles from each other from a predetermined measurement point.

EMBODIMENT FOR CARRYING OUT THE INVENTION

<1. Summary of Each Embodiment>
<1-1. External Appearance and Using Mode>

Figure 1A:
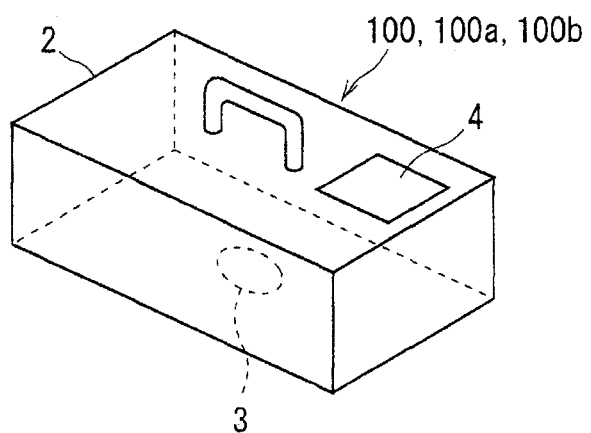
FIGS. 1A and 1B are views showing a multi-angle colorimeter according to each embodiment of the present invention, FIG. 1A being a perspective view showing an external appearance and FIG. 1B being a schematic view for explaining an angular relationship between a central axis of a measuring device body and a measurement plane of a measurement sample.
Figure 1B:
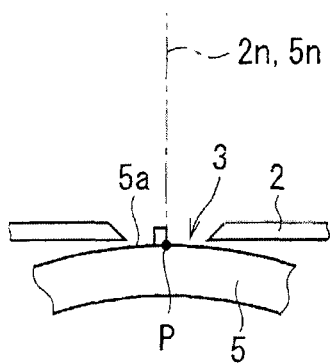

FIGS. 1A and 1B are perspective views showing an external appearance and a schematic view for explaining a positional relationship between a measuring device body and a measurement plane of an object to be measured which are common to a multi-angle colorimeter according to each embodiment of the present invention.

FIG. 1A is a perspective view showing the external appearance of the multi-angle colorimeter. As shown in FIG. 1A a multi-angle colorimeter 100 (100a, 100b) is constituted by a measuring device body 2 taking a shape of a box in which each component to be described below (see FIG. 2) is accommodated. The measuring device body 2 includes a measuring opening 3 formed in a bottom wall and an operation display panel 4 provided in a proper place of a surface and including a display which shows a result of measurement, an operation switch and the like, and constitutes a portable colorimeter.

FIG. 1B is a schematic view for explaining an angle formed by a central axis of a measuring device body of the multi-angle colorimeter 100 (100a, 100b) and a measurement plane of a measurement sample. As shown in FIG. 1B, the measuring opening 3 of the multi-angle colorimeter 100 is turned toward an object to be measured 5 to carry out measurement, and a region of the object to be measured 5 which is opposed to the measuring opening 3 serves as a measurement region 5a. In the measurement, the measuring device body 2 is disposed opposite to a surface of the object to be measured 5 in such a manner that a central axis 2n of the measuring device body 2 (a normal of the measuring opening 3) is coincident with a normal 5n of the measurement region 5a.

In the case in which the object to be measured 5 is a curved surface such as a bumper of a car, it is hard to cause the central axis 2n of the measuring device body 2 to be accurately coincident with the normal 5n of the measurement plane. In general, therefore, the central axis 2n is not coincident with the normal 5n of the measurement plane in many cases and is brought into an inclining state with respect to the normal of the measurement plane. The measurement environment will be hereinafter referred to as an "inclination environment".

<1-2. Basic Functional Configuration of Multi-Angle Colorimeter>

Figure 2:
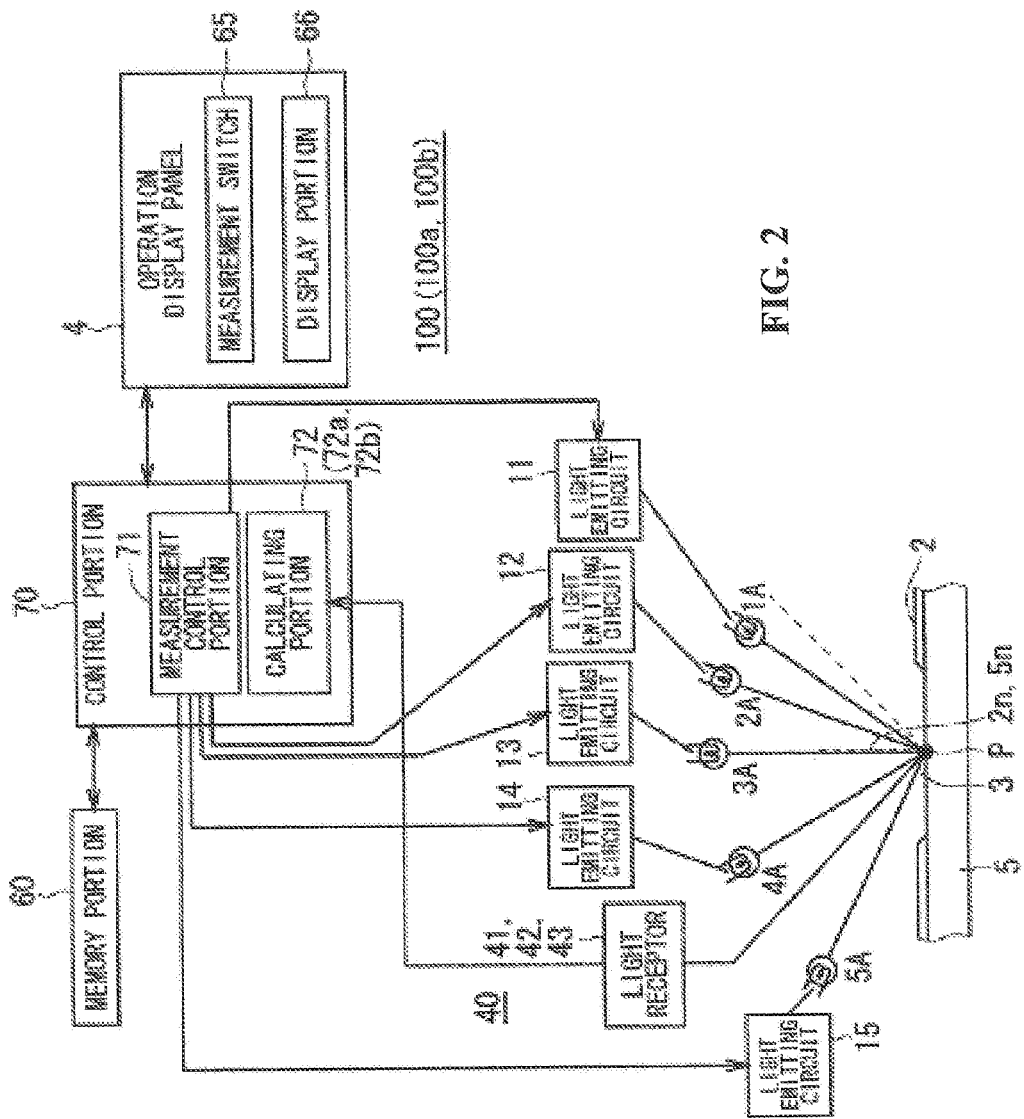
FIG. 2 is a diagram showing an example of a basic functional configuration of the multi-angle colorimeter according to each embodiment of the present invention.

A functional configuration of the multi-angle colorimeter 100 (100a, 100b) according to each embodiment of the present invention will be described by taking a multi-angle colorimeter of a multi-direction illumination and one direction light reception type as an example. FIG. 2 is a diagram showing an example of a basic functional configuration of the multi-angle colorimeter of the multi-direction illumination and one-direction light reception type.

As shown in FIG. 2, a main structure of the multi-angle colorimeter 100 (100a, 100b) includes a plurality of illuminating portions 1A to 5A which are disposed on a virtual reference plane containing a predetermined reference line (the central axis 2n of the measuring device body 2) and carry out light irradiation at different angles toward a predetermined measurement point P defined on the reference line, and a light detecting portion 40 for receiving a light reflected from a measurement plane disposed on the measurement point P and converting the received light into an electrical signal. Moreover, a control portion 70 includes a calculating portion 72 for obtaining a detection value of a light based on the signal and acquiring color information about the measurement plane which is present on the measurement point P based on the detection value. In addition to the structure described above, there are further provided an operation display panel 4, a measurement switch 65, a display portion 66, a memory portion 60 and a measurement control portion 71.

The reference plane is a plane which includes the central axis 2n and is perpendicular to the measurement plane in the case in which the central axis 2n is perpendicular to the measurement plane. This plane will be hereinafter referred to as a "main geometry plane". Moreover, a virtual plane which is orthogonal to the reference plane (a main geometry plane) will be referred to as a "secondary geometry plane".

With reference to FIG. 2, description will be given to a structure and a function which are possessed by the multi-angle colorimeter 100 (100a, 100b).

Each of the illuminating portions 1A to 5A is constituted by a light source comprised of a xenon flash lamp, a regulating plate for regulating a light beam emitted from the light source, and a collimator lens (not shown), for example. Light emitting circuits 11 to 15 for causing the light source to emit a light are provided in the vicinity of the illuminating portions 1A to 5A, respectively.

The light emitting circuits 11 to 15 include a main capacitor for applying a high DC voltage of several hundreds V to an electrode of the light source, for example, a charging circuit for charging the main capacitor, a trigger generating circuit for applying a high AC voltage of several ten thousands V to a trigger electrode comprised of a metallic wire wound in close contact with the light source, and furthermore, include a semiconductor switch element comprised of an IGBT, for example, and a driving circuit for applying a driving voltage to the semiconductor switch element.

When the semiconductor switch element is turned ON and the high AC voltage is instantaneously applied to the trigger electrode through a trigger transformer by a trigger capacitor of the trigger generating circuit in a state in which a high DC voltage is applied to electrodes on both ends of the light source through the main capacitor, the light source is triggered so that a DC current flows from the main capacitor to emit a light. By turning OFF the semiconductor switch element in a desirable timing, then, it is possible to stop the light emission.

The regulating plate is disposed in such a manner that an opening of the regulating plate is coincident with a focal point of the collimator lens, and a light beam emitted from the light source which passes through the opening of the regulating plate is collimated by the collimator lens so that parallel rays are obtained to illuminate the measurement point P of the object to be measured 5.

The light detecting portion 40 has a function for receiving the light reflected from the measurement point P of the object to be measured 5 and converting the received light into an electrical signal, and the details of a functional configuration will be described below.

The operation display panel 4 includes the measurement switch 65 for giving an instruction for starting measurement, the display portion 66 comprised of a liquid crystal display panel for displaying a result of the measurement, for example, and the like.

The memory portion 60 is comprised of an RAM, an EEPROM and the like and temporarily stores the result of the measurement, and furthermore, stores a control program for operating the control portion 70.

The control portion 70 includes an electronic circuit such as a CPU and an A/D converter and includes the measurement control portion 71 and the calculating portion 72 as functional blocks, and controls an operation of each portion in the multi-angle colorimeter 100 (100a, 100b) in accordance with the control program stored in the memory portion 60.

When the measurement switch 65 is operated, the measurement control portion 71 causes respective light sources of the illuminating portions 1A to 5A to sequentially emit a light on a time basis, thereby carrying out colorimetry. Moreover, the measurement control portion 71 causes the display portion 66 to display a result of calculation obtained by the calculating portion 72 as a result of the measurement.

The calculating portion 72 obtains detection values of the lights (spectral reflection characteristics) based on the electrical signal converted by the light detecting portion 40 respectively, and acquires color information (for example, tristimulus values) about the measurement plane which is present on the measurement point P based on the detection values.

<1-3. General Property and Premise Circumstance of Reflected Light Characteristic in Inclination Environment>

As a preparation for describing the details of the multi-angle colorimeter 100 (100a, 100b) according to each embodiment of the present invention, explanation will be given to the general property of a reflected light characteristic to be the premise of each embodiment and circumstances occurring correspondingly, that is, circumstances occurring in the related art.

Figure 3B:
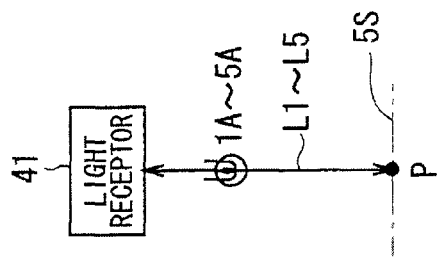
FIGS. 3A and 3B are views for explaining a main geometry plane and a secondary geometry plane through arrangement of an optical system.
Figure 3A:
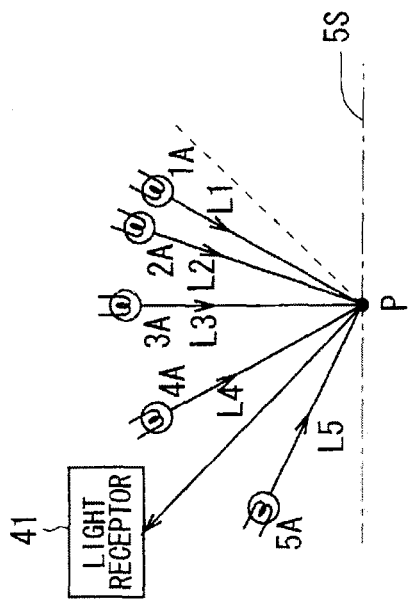

FIGS. 3A and 3B are views for explaining the fact that lights L1 to L5 emitted from the illuminating portions 1A to 5A are reflected by the measurement point P of a measurement plane 5S and are received by a light receptor 41. FIG. 3A is a view seen from the main geometry plane illustrated in FIG. 2 and FIG. 3B is a view seen from the secondary geometry plane.

Description will be given to the circumstances occurring over the secondary geometry plane shown in FIG. 3B.

Figure 4B:
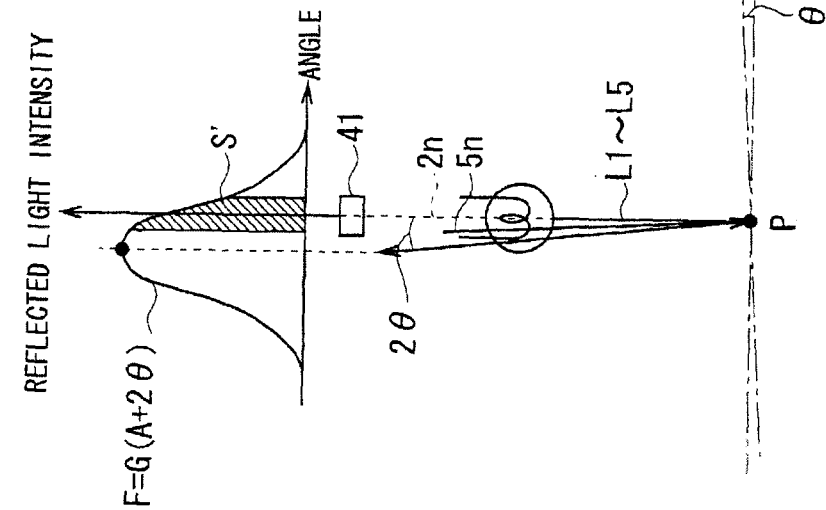
FIGS. 4A and 4B are graphs showing a reflected light intensity, FIG. 4A explains the case of no inclination environment and FIG. 4B explains the case of the inclination environment.
Figure 4A:
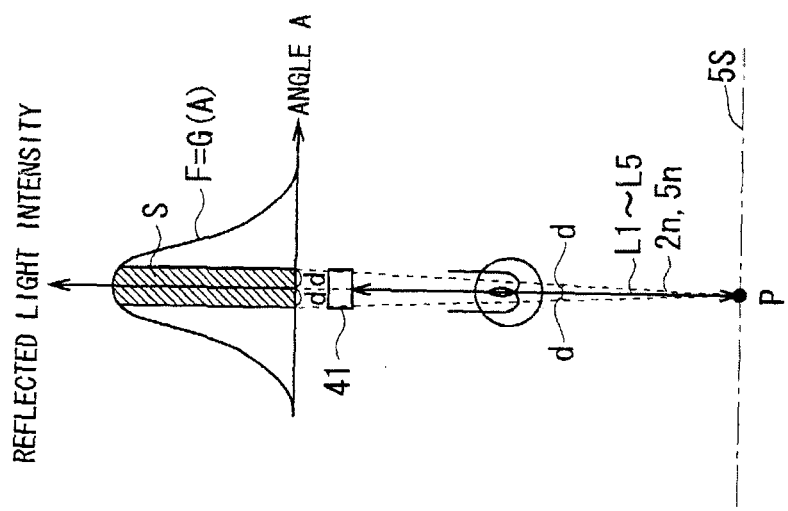

FIGS. 4A and 4B are charts for explaining circumstances occurring due to a shift of the central axis 2n of the measuring device body from the normal 5n of the measurement plane 5S. In the following, a definition is made on the assumption that an angle in a rightward direction of a paper is set to be positive and an angle in a leftward direction of the paper is set to be negative.

FIG. 4A is a graph showing a reflected light intensity in the case of no inclination environment (the central axis 2n of the measuring device body 2 is coincident with the normal 5n of the measurement plane 5S). Moreover, FIG. 4B is a graph showing a reflected light intensity in the case of the inclination environment (the normal 5n is inclined from the central axis 2n by an angle $-\theta$). In the graph, an axis of ordinate indicates a reflected light intensity and an axis of abscissa indicates a shift of an angle from the central axis 2n (which will be hereinafter referred to as an "angle A").

As shown in FIGS. 4A and 4B, the illumination lights L1 to L5 are emitted from the illuminating portions 1A to 5A provided on the central axis 2n and are reflected by the measurement point P of the measurement plane 5S, and are received by the light receptor 41. Regular reflected lights for the illumination lights L1 to L5 sent from the illuminating portions 1A to 5A are emitted in such a direction that they are symmetrical with the illumination lights L1 to L5 with respect to the normal 5n, respectively. In other words, in FIG. 4A, the central axis 2n and the normal 5n are coincident with each other. Therefore, the regular reflected lights for the illumination lights L1 to L5 are emitted in such a direction that the illuminating portions 1A to 5A are positioned. In contrast, in FIG. 4B, the normal 5n is inclined from the central axis 2n in the direction of the angle $-\theta$. Therefore, the regular reflected lights for the illumination lights L1 to L5 are emitted in a direction inclined from the direction in which the illuminating portions 1A to 5A are positioned by an angle of −2θ.

Moreover, a reflected light is emitted in various directions other than the regular reflected light. In consideration of a relationship between the reflected light intensity and the angle A, however, there is a symmetrical attenuating characteristic at angles on both sides having a symmetrical positional relationship around the angle of the regular reflected light as shown in the graphs of FIGS. 4A and 4B. For this reason, the relationship between the reflected light intensity and the angle A can approximate through, as an approximation function F, a simple Gaussian function G (A) in the vicinity of 0° which is comparatively close to the regular reflection in FIG. 4A, while the Gaussian function in FIG. 4B can be approximated by a distribution of G (A +2θ) shifted evenly by the angle of −2θ. A regular reflected light intensity GP is almost G (0) in both of FIGS. 4A and 4B.

On the other hand, the light receptor 41 is positioned in a direction coincident with a direction of a regular reflected light in FIG. 4A, while it is positioned in a direction inclined from the direction of the regular reflected light by an angle of +2θ in FIG. 4B.

In FIG. 4A, therefore, a reflected light quantity S detected by the light receptor 41 is obtained as follows. Herein, ±d represents a width from a center of the light receptor 41 in an angle from the central axis 2n.

$$S = \int_{-d}^{+d} G(A)\, dA \quad \text{[Equation 1]}$$

On the other hand, the following equation is obtained in FIG. 4B.

$$S' = \int_{-d}^{+d} G(A + 2\theta)\, dA \quad \text{[Equation 2]}$$

Accordingly, there is a property that the quantity of the light received by the light receptor 41 is decreased by (S −S') as compared with the case in which the central axis 2n and the normal 5n are coincident with each other (see FIG. 4A) in the case in which the normal 5n of the measurement plane 5S is inclined in a direction of an angle −θ with respect to the central axis 2n of the measuring device body 2 (see FIG. 4B).

In the case in which the measurement is carried out in such a posture that the central axis 2n of the measuring device body 2 is not coincident with the normal 5n of the measurement plane 5S, thus, there is a problem in that the color information about the measurement plane which is present on the measurement point P cannot be obtained correctly.

With the background, in each embodiment according to the present invention, the light detecting portion 40 and the calculating portion 72 (72a, 72b) are improved as compared with the related art. Consequently, the posture error is reduced and the colorimetry for the measurement plane present on the measurement point P is carried out accurately.

Under the preparation, a specific functional configuration and an operation in each embodiment will be described below.

<2. First Embodiment>

The functional configurations of a light detecting portion 40 and a calculating portion 72 in a multi-angle colorimeter 100 according to a first embodiment will be described, and furthermore, a method of correcting a posture error according to the present invention will be described together.

<2-1. Functional Configuration of Light Detecting Portion>

Above all, the functional configuration of the light detecting portion 40 in the multi-angle colorimeter 100 will be described (see FIG. 2).

Figure 5:
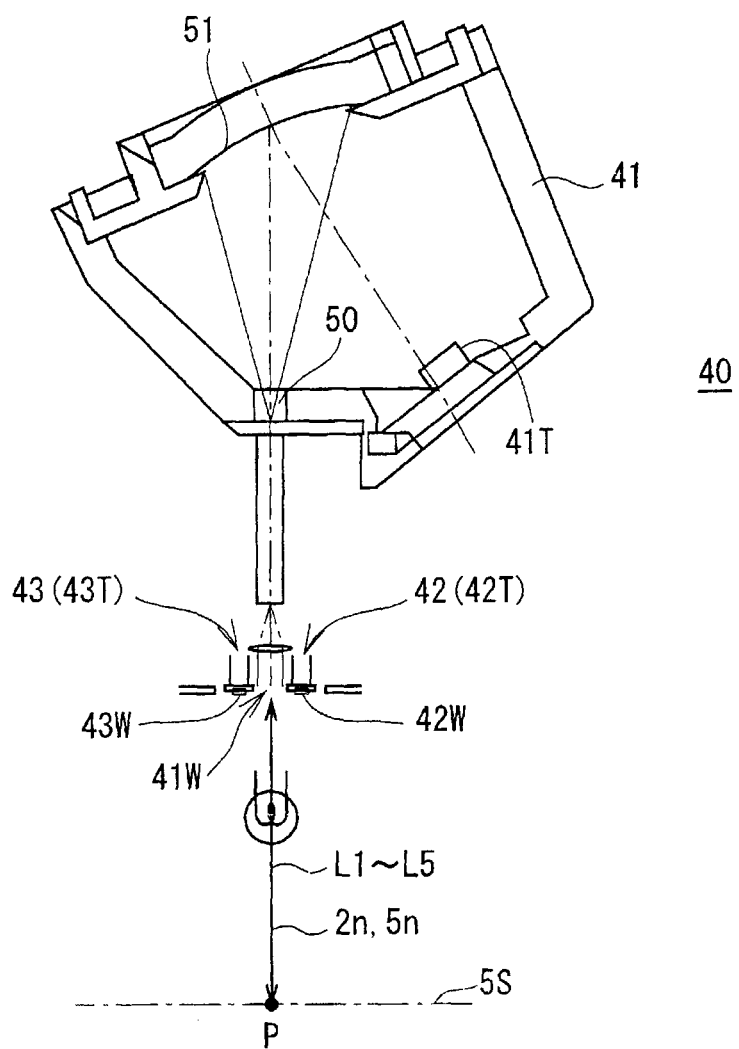
FIG. 5 is a view showing an example of a structure of a light detecting portion at the secondary geometry plane.
Figure 6:
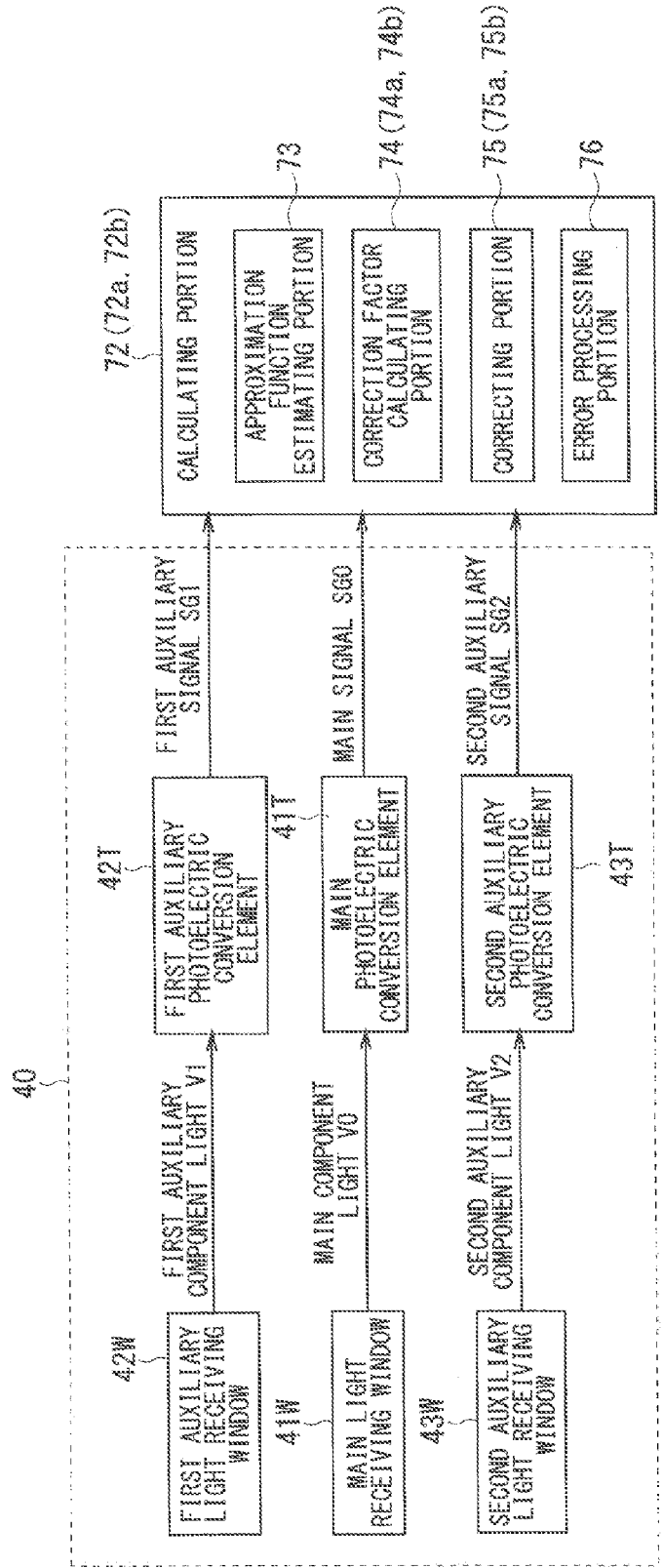
FIG. 6 is a diagram showing functional configurations of the light detecting portion and a calculating portion.

FIG. 5 is a view showing an example of a structure of the light detecting portion 40 in a secondary geometry plane of the multi-angle colorimeter 100 according to the present embodiment, and FIG. 6 is a diagram showing the functional configurations of the light detecting portion 40 and the calculating portion 72.

As an example of the present invention, (I) Arrangement of a plurality of auxiliary light receiving windows on a single side with respect to a main geometry plane, (II) Arrangement of a plurality of auxiliary light receiving windows on both sides with the main geometry plane interposed therebetween, (III) Symmetrical arrangement on both sides particularly in (II), and the like can be executed. In each embodiment according to the present invention, the case of (III) will be described.

As shown in FIG. 5, in the light detecting portion 40, a main light receiving window 41W is disposed in a predetermined position of the main geometry plane, and first and second auxiliary light receiving windows 42W and 43W are disposed on a plane which is opposed to a measurement point P, includes the measurement point P and the predetermined position, and is orthogonal to the main geometry plane (that is, a secondary geometry plane including the measurement point P and the predetermined position). Moreover, the light detecting portion 40 includes a main photoelectric conversion element 41T for receiving a main component light V0 received by the main light receiving window 41W in lights reflected by a measurement plane 5S disposed on the measurement point P and converting the received light V0 into an electrical main signal SG0, and first and second auxiliary photoelectric conversion elements 42T and 43T for receiving first and second auxiliary component lights V1 and V2 received by the first and second auxiliary light receiving windows 42W and 43W in the reflected lights respectively and converting the received lights V1 and V2 into first and second electrical auxiliary signals SG1 and SG2 (see FIGS. 5 and 6). In the present application, the expression of the light receiving window does not specify a particular structure by itself but can include all of structures in which the light reflected by the measurement plane can be incident.

Moreover, it is possible to use a polychromator and the like as the light receptor 41 including the main photoelectric conversion element 41T, for example, and it is possible to use an SPD (Silicon Photodiode) and the like as the auxiliary light receptors 42 and 43 including the first and second auxiliary photoelectric conversion elements 42T and 43T, for example (see FIG. 5).

In other words, the polychromator 41 is a light detecting unit for separating incident rays every wavelength and outputting spectral data corresponding to a light intensity, and includes a concave diffraction grating 51 and a line sensor (a main photoelectric conversion element) 41T. The main component light V0 which is incident from an incidence slit 50 is separated by the concave diffraction grating 51 and is received by the line sensor 41T, and the main component light V0 is converted into the electrical main signal SG0. Also in the SPDs 42 and 43, moreover, the first and second auxiliary component lights V1 and V2 are received by the first and second auxiliary photoelectric conversion elements 42T and 43T and are then converted into the first and second electrical auxiliary signals SG1 and SG2.

Figure 7:
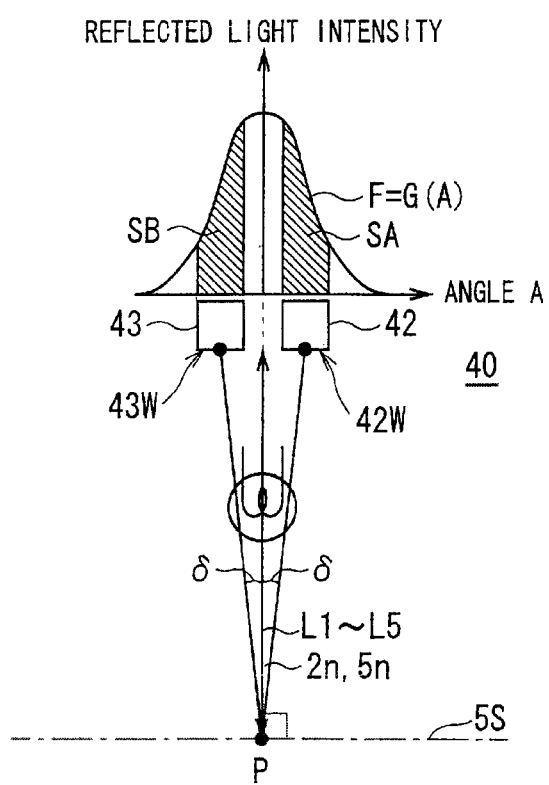
FIG. 7 is a view showing a relationship between a structure of the light detecting portion on the secondary geometry plane and a graph of the reflected light intensity on the secondary geometry plane in the case of no inclination environment.
Figure 8:
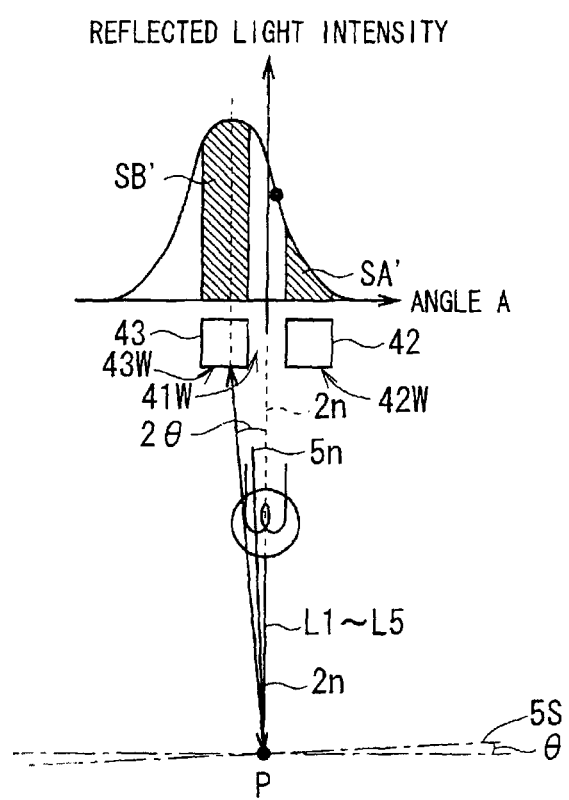
FIG. 8 is a view showing a relationship between the structure of the light detecting portion on the secondary geometry plane and the graph of the reflected light intensity on the secondary geometry plane in the case of the inclination environment.

FIGS. 7 and 8 are graphs showing the structure of the light detecting portion 40 and a reflected light intensity on the secondary geometry plane, and FIG. 7 shows the case of no inclination environment corresponding to FIG. 4A and FIG. 8 shows the case of the inclination environment corresponding to FIG. 4B.

As shown in FIG. 7, the auxiliary light receptors 42 and 43 disposed at an angle of $\pm\delta$ with respect to a central axis 2$n$ obtain reflected light quantities which are equivalent to slash regions SA and SB of a Gaussian function G (A) through the first and second auxiliary light receiving windows 42W and 43W. Specifically, a reflected light quantity SA of the first auxiliary component light V1 which is detected by the auxiliary light receptor 42 is obtained as follows.

$$SA = \int_{\delta-d}^{\delta+d} G(A)\,dA \qquad \text{[Equation 3]}$$

A reflected light quantity SB of the second auxiliary component light V2 which is detected by the auxiliary light receptor 43 is obtained as follows.

$$SB = \int_{-\delta-d}^{-\delta+d} G(A)\,dA \qquad \text{[Equation 4]}$$

A width of a light receiving range from a center of the auxiliary light receptor 42 (or 43) may be different from a width from a center of the light receptor 41. For simplicity of the description, the width of the light receiving range from the center of the auxiliary light receptor 42 (or 43) is set to be a width at an angle of $\pm d$ from the central axis 2$n$ in the same manner as the light receptor 41.

By the Equations 3 and 4, a relationship of SA=SB is established in the case of no inclination environment. On the other hand, in FIG. 8, the Gaussian function has a distribution of G (A+2θ) shifted uniformly at an angle of −2θ in the case in which the normal 5$n$ of the measurement plane 5S is inclined in a direction of an angle −θ with respect to the central axis 2$n$ of the measuring device body 2. Therefore, a reflected light quantity SA' of the first auxiliary component light V1 which is detected by the auxiliary light receptor 42 is obtained as follows.

$$SA' = \int_{\delta-d}^{\delta+d} G(A+2\theta)\,dA \qquad \text{[Equation 5]}$$

As shown in FIGS. 7 and 8, a relationship of SA>SA' is established. For this reason, it is apparent that a light is received in a smaller quantity by the auxiliary light receptor 42 than that in the case of no posture error when the posture error is made. On the other hand, a reflected light quantity SB' of the second auxiliary component light V2 which is detected by the auxiliary light receptor 43 is obtained as follows.

$$SB' = \int_{-\delta-d}^{-\delta+d} G(A+2\theta)\,dA \qquad \text{[Equation 6]}$$

As shown in FIGS. 7 and 8, a relationship of SB<SB' is established. For this reason, it is apparent that a light is received in a larger quantity by the auxiliary light receptor 43 than that in the case of no posture error when the posture error is made.

In the case in which the posture error is made, thus, a relationship between an inclination quantity thereof and the light receiving quantities of the auxiliary light receptors 42 and 43 is equivalent to an increasing function of the inclination quantity for one of the respective light receiving quantities of the auxiliary light receptors 42 and 43 and is equivalent to a decreasing function of the inclination quantity for the other in the present embodiment. For this reason, the respective light receiving quantities of the auxiliary light receptors 42 and 43 have an almost one to one relationship with the inclination quantity.

In the correction of the posture error according to the embodiment of the present invention, therefore, a measured value of the main component light V0 is corrected by utilizing the relationship between the inclination quantity and the light receiving quantity of the reflected light. Thus, this reduces the influence of the posture error.

<2-2. Functional Configuration of Calculating Portion>

Subsequently, description will be given to a functional configuration of the calculating portion 72 in the multi-angle colorimeter 100 (see FIG. 2).

As shown in FIG. 6, in the calculating portion 72, the main signal SG0 is corrected based on the first and second auxiliary signals SG1 and SG2 to obtain color information about the measurement plane which is present on the measurement point P. The calculating portion 72 includes an approximation function estimating portion 73, a correction factor calculating portion 74, a correcting portion 75, and an error processing portion 76.

Figure 9:
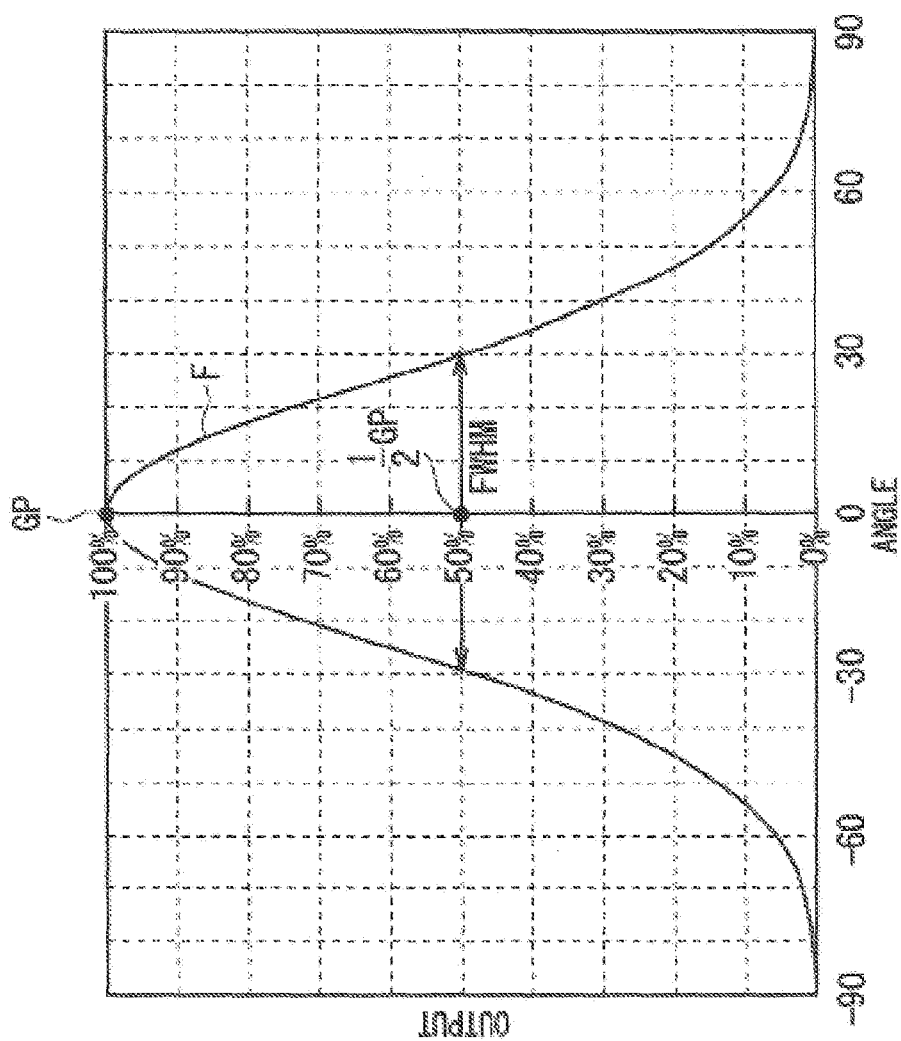
FIG. 9 is a chart illustrating an approximation function for the reflected light intensity.

The approximation function estimating portion 73 obtains an approximation function for approximating to a directional dependency of a reflected light. Specifically, lights L1 to L5 emitted from a plurality of illuminating portions 1A to 5A are reflected at other angles in addition to a central peak position on the measurement point P of the measurement plane 5S. In the reflected lights, an intensity distribution of a reflected light in a secondary geometry plane is estimated as an approximation function F. More specific description will be given by taking, as an example, the case in which the light receptor 41 receives the reflected light from any of the illuminating portions 1A to 5A which is disposed in a close position to a regular reflecting position of the light receptor 41 with respect to the measurement point P. In the angular distribution on the secondary geometry plane, it can be supposed that a light reflected regularly by a brilliant material is predominant in the vicinity of 0° which is close to the regular reflection. Therefore, it is possible to carry out approximation by a Gaussian distribution shown in FIG. 9. In other words, it can be estimated that the approximation function F has a Gaussian distribution shifted uniformly at an angle of +2θ in the case in which the normal 5$n$ of the measurement plane 5S is inclined in a direction of the angle −θ with respect to the central axis 2$n$ of the measuring device body 2 from the foregoing. Therefore, a Gauss peak GP, a Gauss half value width FWHM and a shift quantity 2θ are found as three unknown quantities to estimate the approximation function F.

When the approximation function F is to be found, there are the three unknown quantities and it is impossible to perfectly set a posture error θ=0 in measurement. For this reason, θ is assumed to be finite and is thus put into an equation to generate three different simultaneous equations from three measured values acquired by the light receptor 41 and the auxiliary light receptors 42 and 43. Then, these simultaneous equations are solved to find a specific form of the approximation function F.

Figure 14A:
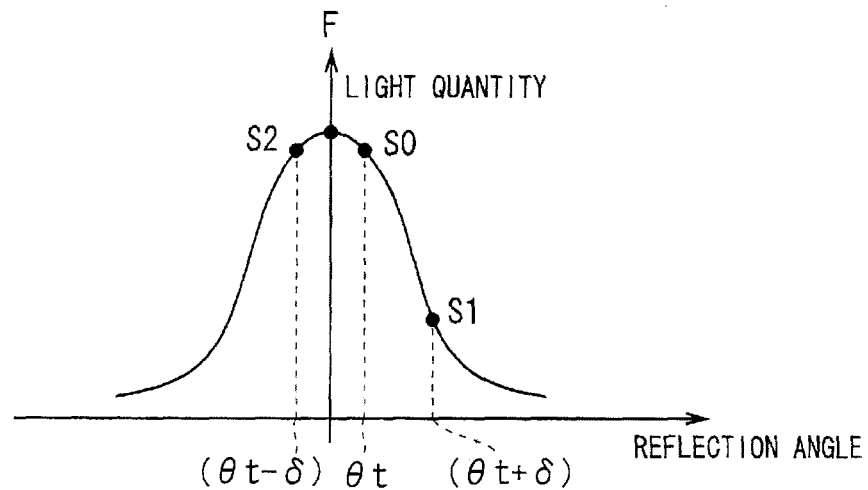
FIGS. 14A to 14C are charts illustrating a correction approximation function.

The process is illustrated in FIG. 14A, and the approximation function F is subjected to fitting on three points determined by measured values S0, S1 and S2, and positions corresponding to a posture error θt of the light receptor 41 at that time and posture angles (θt±δ) of the auxiliary light receptors 42 and 43 so that the specific form of the approximation function F is determined.

In order to solve the simultaneous equations, a solution may be strictly calculated based on the equation or the sum of squares of a difference between the approximation function F and an actual measurement value may be set to be an evaluation value to approximately find such a numerical solution that the evaluation value is minimized.

A ratio Sp/S0 of a peak value Sp of the approximation function F to a current measured value S0 is set to be a correction factor C.

The correcting portion 75 carries out a calculation for correcting a non-corrected measured value of the electrical main signal SG0 by using the correction factor C thus obtained through the correction factor calculating portion 74.

In the case in which the light receptor 41 receives a reflected light from any of the illuminating portions 1A to 5A that is disposed in a distant position from a regular reflecting position of the light receptor 41 with respect to the measurement point P, an approximation function corresponding to the position is preset and is thus used to find the correction factor C. Consequently, it is possible to carry out a calculation for the correction.

<2-3. Example of Control of Multi-Angle Colorimeter>

Subsequently, description will be given to the measuring operations of the multi-angle colorimeter 100. The control portion 70 automatically executes these operations in accordance with a program stored in the memory portion 60.

Figure 10:
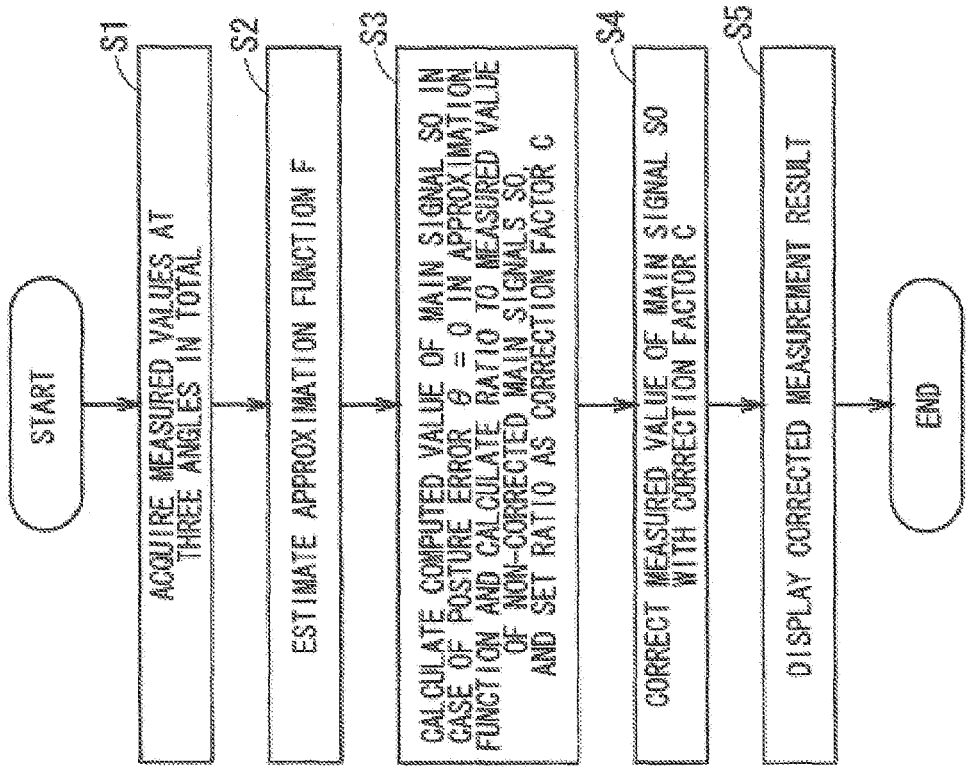
FIG. 10 is a flow chart showing an operation flow of a multi-angle colorimeter according to a first embodiment.

FIG. 10 is a flow chart illustrating a flow of the operation to be implemented in the multi-angle colorimeter 100. Since the individual functions of the respective portions have already been described, only a whole flow will be explained. First of all, the present operation flow is started depending on a manipulation for the measurement switch 65 by a user, for example, and the processing proceeds to Step S1 of FIG. 10.

At the Step S1, the lights L1 to L5 are emitted from the plurality of the illuminating portions 1A to 5A. Then, the light reflected by the measurement point P of the measurement plane 5S is detected as the main component light V0 in the light receptor 41 through the main light receiving window 41W, and furthermore, is detected as the first and second auxiliary component lights V1 and V2 in the auxiliary light receptors 42 and 43 through the first and second auxiliary light receiving windows 42W and 43W. Furthermore, the main component light V0 is converted into the electrical main signal SG0 by the main photoelectric conversion element 41T, and the first and second auxiliary component lights V1 and V2 are converted into the first and second electrical auxiliary signals SG1 and SG2 by the first and second auxiliary photoelectric conversion elements 42T and 43T. Thus, three measured values are acquired.

At Step S2, the approximation function estimating portion 73 estimates a parameter value expressing the specific form of the approximation function F by using the three measured values of the electrical main signal SG0 and the first and second electrical auxiliary signals SG1 and SG2 which are acquired. By the principle described with reference to FIG. 14A, then, the specific form of the approximation function F is determined and is thus stored in the memory portion 60.

At Step S3, the correction factor calculating portion 74 obtains the specific value of the correction factor C for correcting the electrical main signal SG0 based on the specific form of the approximation function F.

At Step S4, the correcting portion 75 carries out a calculation for correcting the measured value of the non-corrected electrical main signal SG0 by using the correction factor C. Specifically, the value of the electrical main signal SG0 is multiplied by the correction factor C to acquire the value of the corrected electrical main signal Sp as a value obtained after correcting the electrical main signal SG0.

At Step S5, the measurement control portion 71 calculates color information about the measurement plane present on the measurement point P by using the value of the corrected electrical main signal Sp acquired by the correcting portion 75 and displays the color information as a measurement result on the display portion 66. Thus, the present operation flow is ended.

As described above, the electrical main signal SG0 is corrected based on information about light components obtained from the first and second auxiliary light receiving windows 42W and 43W. Also in the case of the inclination environment, therefore, it is possible to carry out proper colorimetry.

<3. Second Embodiment>
<3-1. Functional Configuration of Multi-Angle Colorimeter>

Although a basic functional configuration of a multi-angle colorimeter 100a according to a second embodiment of the present invention is almost the same as that in the first embodiment as shown in FIG. 2, a function of a calculating portion 72a is different from that in the first embodiment. Since the residual configurations are the same as those of the device according to the first embodiment, only different respects will be described.

As shown in FIG. 6, an approximation function estimating portion 73 is provided as the function of the calculating portion 72a in the same manner as in the first embodiment, and functions of a correction factor calculating portion 74a and a correcting portion 75a are different.

The correction factor calculating portion 74a calculates a ratio R of measured values of first and second electrical auxiliary signals SG1 and SG2, in the case where a posture error occurs, based on an approximation function F obtained by the approximation function estimating portion 73, and collectively sets a relationship between a plurality of concrete values R1, R2, . . . of the ratio R of the measured values and values C1, C2, . . . of the correction factor C corresponding thereto respectively into a table as shown in FIG. 11 and thus stores the table in a memory portion 60 in a look-up table format. In FIG. 11, for easy understanding, values θ1, θ2, . . . of a posture error θ corresponding thereto are also described in the table. In order to correct a main component light V0, however, it is not necessary to use the value itself of the posture error θ. For this reason, it is possible to omit registration of the value of the posture error θ in the table.

The correcting portion 75*a* calculates the ratio R of the measured values of the first and second electrical auxiliary signals SG1 and SG2 obtained in each measurement, reads the posture error θ and the correction factor C with respect to the ratio R of the measured values in each measurement by referring to the correction table stored in the memory portion 60 (see FIG. 11), and furthermore, carries out a calculation for correcting a measured value of the non-corrected main component light V0 by using the correction factor C.

For example, in the case in which the specific value of the ratio R of the measured values is R3 in the correction table of FIG. 11, a posture error value θ3 and a correction factor value C3 are read as the posture error θ and the correction factor C which correspond to the ratio R of the measured values.

<3-2. Example of Control of Multi-Angle Colorimeter>

Subsequently, description will be given to the measuring operations of the multi-angle colorimeter 100*a*. A control portion 70 automatically executes these operations in accordance with a program stored in the memory portion 60.

Figure 12:
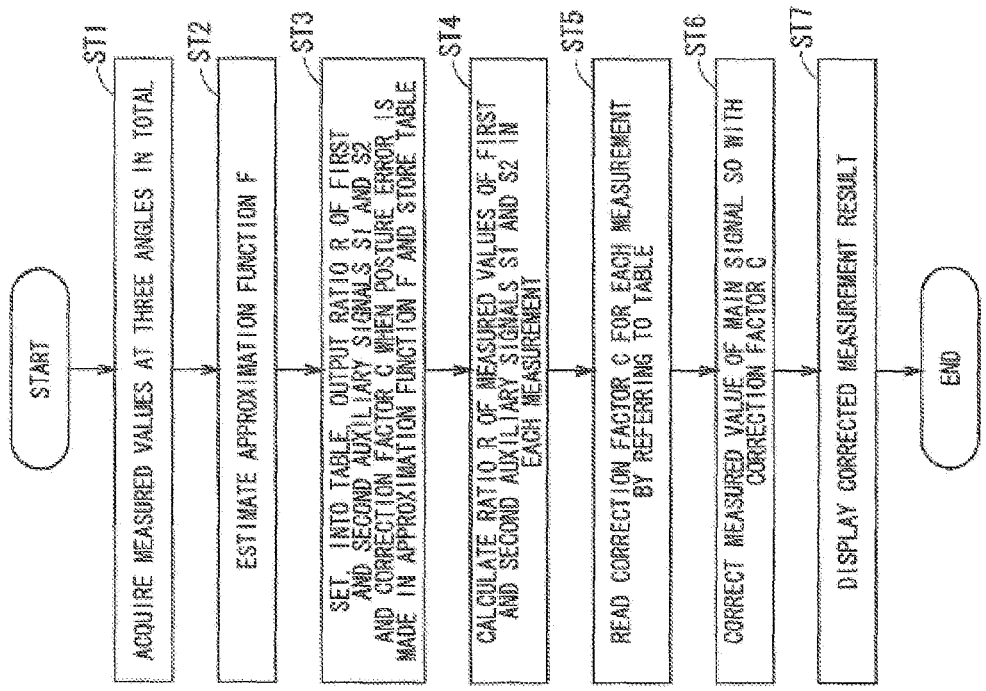
FIG. 12 is a flow chart showing an operation flow of a multi-angle colorimeter according to a second embodiment.

FIG. 12 is a flow chart illustrating a flow of the operation to be implemented in the multi-angle colorimeter 100*a*. Since the individual functions of the respective portions have already been described, only a whole flow will be explained. First of all, the present operation flow is started depending on a manipulation for the measurement switch 65 by a user, for example, and the processing proceeds to Step ST1 of FIG. 12.

At the Step ST1, lights L1 to L5 are emitted from illuminating portions 1A to 5A. Then, the light reflected by a measurement point P of a measurement plane 5S is detected as the main component light V0 in a light receptor 41 through a main light receiving window 41W, and furthermore, is detected as first and second auxiliary component lights V1 and V2 in auxiliary light receptors 42 and 43 through first and second auxiliary light receiving windows 42W and 43W. Furthermore, the main component light V0 is converted into an electrical main signal SG0 by a main photoelectric conversion element 41T, and the first and second auxiliary component lights V1 and V2 are converted into first and second electrical auxiliary signals SG1 and SG2 by first and second auxiliary photoelectric conversion elements 42T and 43T. Thus, three measured values are acquired.

At Step ST2, by the principle described with reference to FIG. 14A, the approximation function estimating portion 73 causes the approximation function F to be concrete by using the three measured values of the electrical main signal SG0 and the first and second electrical auxiliary signals SG1 and SG2 which are acquired, and stores a parameter expressing the approximation function F in the memory portion 60.

At Step ST3, the correction factor calculating portion 74 creates the correction table (FIG. 11) expressing the correction factor C of the electrical main signal SG0 numerically based on the approximation function F and stores the correction table in the memory portion 60.

Figure 14B:
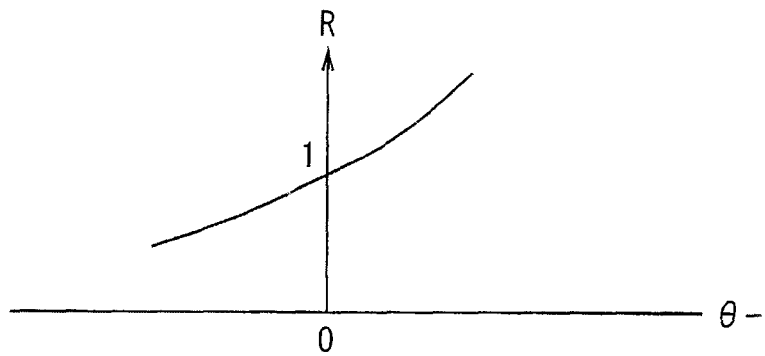

More detailed description will be given. The correction factor calculating portion 74 specifies, as shown in FIG. 14B, a relationship as to how a ratio of measured values S1 and S2 of R =S2 / S1 is varied depending on the value of the posture error angle θ from the concrete format of the approximation function F, and uses the relationships of FIGS. 14A and 14B to obtain a corrected approximation function K (R) for defining a ratio of a peak value Sp of the approximation function F to a measured value S0 of a light receptor 41 with the radio R set to be a parameter (see FIG. 14C). The peak value Sp of the approximation function F is equivalent to an output value of the electrical main signal SG0 in the case of no posture error (θ=0). A relationship of the corrected approximation function K (R) is stored as a numerical table (see FIG. 11) in the memory portion 60.

At Step ST4, the correcting portion 75*a* calculates the ratio R of the measured values of the first and second electrical auxiliary signals SG1 and SG2.

At Step ST5, the correcting portion 75*a* reads the correction factor C corresponding to the value of the ratio R by referring to the correction table stored in the memory portion 60.

At Step ST6, the correcting portion 75*a* carries out a calculation for correcting a measured value S0 of the electrical main signal SG0 by using the correction factor C. In other words, the measured value S0 is multiplied by the value of the correction factor C read from a relevant row of the correction table. Consequently, it is possible to obtain the value Sp of the electrical main signal SG0 corresponding to a state of the posture error θ=0.

At Step ST7, a measurement control portion 71 calculates color information about the measurement plane present on the measurement point P by using the measured value of the electrical main signal SG0 corrected by the correcting portion 75*a* and displays the color information as a measurement result on the display portion 66. Thus, the present operation flow is ended.

As described above, the electrical main signal SG0 is corrected based on information about light components obtained from the first and second auxiliary light receiving windows 42W and 43W. Also in the case of the inclination environment, therefore, it is possible to carry out proper colorimetry.

As a difference between the first and second embodiments, it is desirable that the approximation function F should be calculated by following the process of the Steps ST1 to ST5 every measurement as in the first embodiment if high correction precision is required. When the approximation function F is to be updated for each measurement, it is sufficient to simply know the peak value Sp of the approximation function at that time. For this reason, it is enough even if the correction table for defining the correction factor C depending on various values of the ratio R is not created. On the other hand, in the case in which a measurement time is required to be shortened, the correction precision conforms thereto. However, it is desirable to store the correction table as in the second embodiment and to read the correction table every measurement to carry out the correction. It is possible to store the approximation function F in the memory portion 60 in first measurement and to read the correction table to carry out the correction in the measurement of a measuring target having a painting material of the same type in second measurement and thereafter. Specifically, the Steps ST2 and ST3 are skipped in the flow of FIG. 12. For this reason, whether "a mode for calculating the approximation function F every measurement" or "a mode for creating and storing the correction table" is preferable as default is varied depending on a user's request.

<4. Third Embodiment>

In the case in which a posture error exceeding an acceptable limit is made, there is also a possibility that the measurement precision might be poorer due to forcible execution of the correction. Therefore, a multi-angle colorimeter 100*b* which will be described below has a function for displaying an error and promoting a user to carry out measurement again when it is estimated that the posture error exceeds a certain value.

<4-1. Functional Configuration of Multi-Angle Colorimeter>

Although a basic functional configuration of the multi-angle colorimeter 100b according to a third embodiment of the present invention is almost the same as that in the first embodiment as shown in FIG. 2, a function of a calculating portion 72b is different from that in the first embodiment. Since the residual configurations are the same as those of the device according to the first embodiment, only different respects will be described.

As shown in FIG. 6, an approximation function estimating portion 73 is provided as the function of the calculating portion 72b in the same manner as in the first embodiment, and functions of a correction factor calculating portion 74b and a correcting portion 75b are different.

Figure 14C:
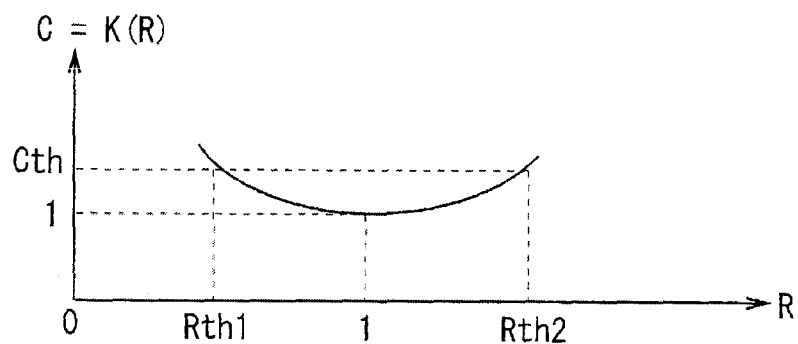

The correction factor calculating portion 74b calculates a ratio R of measured values of first and second electrical auxiliary signals SG1 and SG2, in a case where a posture error occurs, based on an approximation function F obtained by the approximation function estimating portion 73 and collectively sets the ratio R of the output values and a correction factor C into a table as shown in FIG. 11, and stores the table in a memory portion 60. At the same time, a threshold for defining a correctable range of a posture error is predetermined experimentally, and the threshold is stored as a known value in the memory portion 60. The threshold may be an upper limit threshold Cth of the correction factor C or a set of a lower limit threshold Rth1 and an upper limit threshold Rth2 of the ratio R corresponding to the upper limit threshold Cth as shown in FIG. 14C. The thresholds are stored as known values in the memory portion 60 (Rth1<1<Rth2).

The correcting portion 75b calculates the ratio R of the measured values of the first and second electrical auxiliary signals SG1 and SG2 obtained in each measurement, compares the ratio R with the thresholds Rth1 and Rth2, reads the correction factor C with respect to the ratio R of the measured values in each measurement by referring to the correction table stored in the memory portion 60 when the ratio R is present between the thresholds Rth1 and Rth2 (when the ratio R approximates to "1") or the correction factor C is smaller than the threshold Cth, and carries out a calculation for correcting a measured value of a non-corrected main component light V0 by using the correction factor C. When the ratio R is smaller than the lower limit threshold Rth1 or exceeds the upper limit threshold Rth2, that is, when the ratio R is not close to "1", it is decided that a posture error is excessively great and an error is displayed on a display portion 66, and a user is promoted to change a posture of the colorimeter and to then carry out remeasurement. The error display may be visual display or an alarm sound.

When the threshold Cth of the correction factor C is used, the correction factor C is once read from the correction table and the error display is carried out when the correction factor C is greater than the threshold Cth.

In other words, in the present embodiment, the predetermined threshold(s) Rth1 and Rth2 (Cth) for defining the effective range of the correction of an electrical main signal SG0 are prestored and the ratio R itself of the measured values of the first and second electrical auxiliary signals SG1 and SG2 obtained in each measurement or the correction factor C corresponding to the ratio R is used as an index value corresponding to the ratio R of the measured values, and the index value and the threshold(s) Rth1 and Rth2 (Cth) are compared with each other and error processing is carried out if the index value departs from the effective range of the correction.

<4-2. Example of Control of Multi-Angle Colorimeter>

Subsequently, description will be given to the measuring operations of the multi-angle colorimeter 100b. A control portion 70 automatically executes these operations in accordance with a program stored in the memory portion 60.

Figure 13:
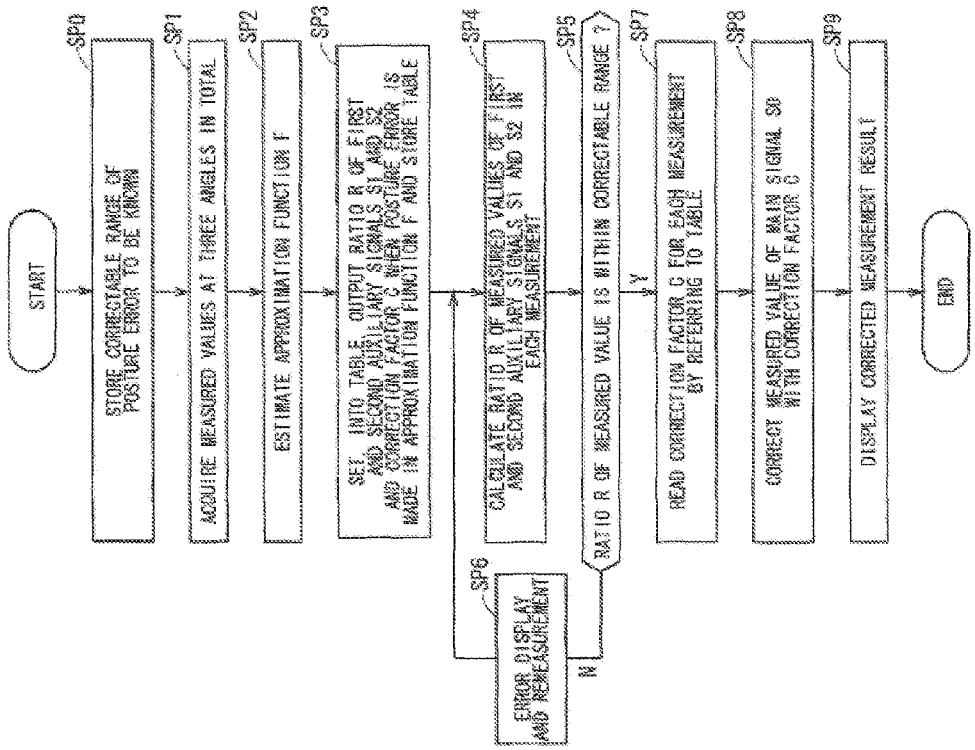
FIG. 13 is a flow chart showing an operation flow of a multi-angle colorimeter according to a third embodiment.

FIG. 13 is a flow chart illustrating a flow of the operation to be implemented in the multi-angle colorimeter 100b. Since the individual functions of the respective portions have already been described, only a whole flow will be explained.

At a previous preparation step SP0, the correction factor calculating portion 74 stores the thresholds Rth1 and Rth2 (or the threshold Cth) for defining a correctable range of a posture error as known values in the memory portion 60. When certain values are always used as these thresholds, the values of the thresholds may be stored in manufacture or shipment of the colorimeter. When the thresholds are made variable depending on a type of a measurement plane, a user may utilize an operation display panel 4 or the like to input the values of the thresholds, thereby storing them variably.

In the following, in a specific measuring operation, the present operation flow is first started depending on a manipulation for a measurement switch 65 by the user, for example, and the processing proceeds to Step SP1.

Steps SP1 to SP4 are the same as the Steps ST1 to ST4 in FIG. 12, respectively.

At Step SP5, the correcting portion 75b decides whether or not the read correction factor C can be utilized, or it is in a correctable range, based on the comparison between the ratio R and the thresholds Rth1 and Rth2. If it is in the correctable range, the processing proceeds to Step SP7. On the other hand, if it is out of the correctable range, an error is displayed in the display portion 66 at Step SP6 and the user is promoted to change the posture of the colorimeter and to carry out remeasurement. After the user carries out the measurement again, the processing returns to the Step SP4.

If it is decided at the Step S5 that it is in the correctable range in first measurement or remeasurement, the processing proceeds to the Step SP7. Steps SP7 to SP9 are the same as the ST5 to ST7 in FIG. 12, respectively.

When the threshold Cth of the correction factor C is to be used, it is sufficient to execute the Step SP7 prior to the Step SP5, to once read the correction factor C from the correction table and to compare the correction factor C with the threshold Cth, and to then make a branch into the Step SP6 or the Step SP8 based on a result of the comparison.

As described above, in the present embodiment, the electrical main signal SG0 is corrected based on the information about the light component obtained from the first and second auxiliary light receiving windows 42W and 43W. Also in the case of an inclination environment, therefore, it is possible to carry out proper colorimetry, and furthermore, to prevent false measurement due to erroneous use of a result of the measurement in such a posture that proper correction is hard to perform.

<5.Variant>

Although the embodiments according to the present invention have been described above, the present invention is not restricted to the embodiments but various changes can be made.

Although the multi-angle colorimeter according to the present embodiment has been described to have the multi-direction illumination and one direction light reception type, one direction illumination and multi-direction light reception type can also be applied in the same manner.

Although there has been employed the method of carrying out symmetrical disposition on both sides of the main light receiving window with the main geometry plane interposed therebetween in the present embodiment, it is also possible to employ a method of asymmetrically disposing the auxiliary light receptors 42 and 43 on the secondary geometry plane with respect to the central axis $2n$ or a method of disposing a plurality of sensors on a single side with respect to a central axis $2n$. Moreover, three auxiliary light receptors or more may be provided. If the auxiliary light receptor is provided in such a manner that it is opposed to a measurement point at an equal angle to an angle formed by the main light receiving window when a projection to the main geometry plane is carried out, that is, a projection component to the main geometry plane has an equal angle to the angle of the main light receiving window, a position is optional.

Although the Gaussian function is used as the approximation function F in the present embodiment, it is also possible to employ a structure in which a function approximating with high precision approximates to a reflection angle characteristic of a sample and auxiliary sensors in accordance with the number of undecided numbers of the function −1 are provided.

A structure of the multi-angle colorimeter described above includes (a) an illuminating portion disposed on a virtual reference plane including a predetermined reference line and carrying out light irradiation toward a predetermined measurement point defined on the reference line, (b) a light detecting portion, the light detecting portion including a main light receiving window disposed in a predetermined position on the reference plane, a plurality of auxiliary light receiving windows disposed on a plane which includes the predetermined position and the predetermined measurement point and is orthogonal to the reference plane, and opposed to the measurement point respectively, a main photoelectric conversion element for receiving a main component light received by the main light receiving window in a reflected light from a measurement plane disposed on the measurement point and converting the main component light into an electrical main signal, and a plurality of auxiliary photoelectric conversion elements for receiving a plurality of auxiliary component lights received by the plurality of auxiliary light receiving windows in the reflected light and converting the plurality of auxiliary component lights into a plurality of electrical auxiliary signals, and (c) a calculating portion for correcting the electrical main signal based on the plurality of electrical auxiliary signals, thereby obtaining color information about the measurement plane which is present on the measurement point.

Moreover, the multi-angle colorimeter includes an approximation function estimating portion for finding an approximation function which approximates to a directional dependency of the reflected light by using the electrical main signal and the plurality of electrical auxiliary signals, a correction factor calculating portion for calculating a correction factor based on the approximation function found by the approximation function estimating portion, and a correcting portion for carrying out a calculation for correcting the electrical main signal by using the correction factor obtained by the correction factor calculating portion. The correction factor calculating portion calculates a ratio of measured values of the plurality of electrical auxiliary signals based on the approximation function found by the approximation function estimating portion and stores the ratio of the measured values and the correction factor as a table, and the correcting portion calculates a ratio of measured values of a plurality of electrical auxiliary signals obtained in each measurement, reads a correction factor for the ratio of the measured values by referring to the table, and furthermore, corrects a measured value of the electrical main signal by using the correction factor.

Furthermore, the multi-angle colorimeter includes a storing portion 60 for storing a predetermined threshold for defining an effective range for the correction of the main signal by the correcting portion, and the correcting portion includes an error processing portion 76 for comparing an index value corresponding to the ratio of the measured values of the plurality of auxiliary signals with the predetermined threshold and carrying out error processing if the index value departs from the effective range.

In addition, the multi-angle colorimeter includes a plurality of illuminating portions disposed on the reference plane respectively and carrying out light irradiation at different angles from each other toward the measurement point.

Moreover, as shown in FIG. 15, the multi-angle colorimeter 100(100c) includes a light emitting circuit 80, a plurality of main light receiving receptors 110, 120 disposed on the reference plane respectively and receiving lights reflected at different angles from each other from the measurement point, and includes a plurality of auxiliary light receiving windows for the plurality of main light receiving windows, respectively.

According to the multi-angle colorimeter including the structure, the electrical main signal is corrected based on the information about the light component obtained from the plurality of auxiliary light receiving windows disposed on the plane which includes the predetermined position and the measurement point and is orthogonal to the reference plane. Even if the reference plane is inclined from the normal of the measurement plane, therefore, it is possible to carry out proper colorimetry.

Alternatively, the multi-angle colorimeter carries out the error processing if the index value corresponding to the ratio of the measured values of the plurality of electrical auxiliary signals obtained in each measurement is out of the effective range of the correction. Consequently, it is possible to promote a user to carry out remeasurement. In measurement exceeding an acceptable limit, thus, it is not necessary to forcibly carry out the correction.

DESCRIPTION OF THE NUMERALS 100, 100a to 100e multi-angle colorimeter
2 measuring device body
$2n$ central axis
3 measuring opening
5 object to be measured
$5n$ normal
1A to 5A illuminating portion
40 light detecting portion
60 memory portion
66 display portion
70 control portion
71 measurement control portion
73 approximation function estimating portion
72, 72a, 72b calculating portion
74, 74a, 74b correction factor calculating portion
75, 75a, 75b correcting portion
SG0 electrical main signal
Sp corrected main signal C correction factor
SG1 first electrical auxiliary signal
SG2 second electrical auxiliary signal
R ratio of measured values of first and second electrical auxiliary signals
V0 main component light
V1 first auxiliary component light
V2 second auxiliary component light
F approximation function of light receiving signal setting posture error θ as variable
K (R) correction approximation function setting auxiliary signal ratio R as variable

The invention claimed is:

1. A multi-angle colorimeter comprising:
   (a) a plurality of illuminating means disposed on a virtual reference plane including a predetermined reference line and carrying out light irradiation at different angles from each other toward a predetermined measurement point on said reference line;
   (b) a light detector comprising:
      a main light receiving window disposed in a predetermined position on said reference plane;
      a plurality of auxiliary light receiving windows disposed on a plane which includes said predetermined position and said predetermined measurement point and is orthogonal to said reference plane, and opposed to said measurement point respectively;
      a main photoelectric conversion means for receiving a main component light received by said main light receiving window in a reflected light of said light irradiation from a measurement plane disposed on said measurement point and for converting said main component light into an electrical main signal; and
      a plurality of auxiliary photoelectric conversion means for receiving a plurality of auxiliary component lights received by said plurality of auxiliary light receiving windows in the reflected light of said light irradiation and for converting said plurality of auxiliary component lights into a plurality of electrical auxiliary signals, and
   (c) a calculating means for correcting a posture error, of said reference plane from the normal of said reference plane, of said electrical main signal based on said plurality of electrical auxiliary signals, thereby obtaining color information about said measurement plane which is present on said measurement point.

2. The multi-angle colorimeter according to claim 1, wherein said calculating means comprises:
   an approximation function estimating means for finding an approximation function which approximates to a directional dependency of said reflected light by using said electrical main signal and said plurality of electrical auxiliary signals;
   a correction factor calculating means for calculating a correction factor based on said approximation function found by said approximation function estimating portion; and
   a correcting means for carrying out a calculation for correcting said electrical main signal by using said correction factor obtained by said correction factor calculating means.

3. The multi-angle colorimeter according to claim 2, wherein said correction factor calculating means calculates a ratio of measured values of said plurality of electrical auxiliary signals based on said approximation function found by said approximation function estimating means and storing said ratio of said measured values and said correction factor as a table, and
   wherein said correcting means calculates a ratio of measured values of a plurality of electrical auxiliary signals obtained in each measurement, reads a correction factor for said ratio of said measured values by referring to said table, and furthermore, corrects a measured value of said electrical main signal by using said correction factor.

4. The multi-angle colorimeter according to claim 3, further comprising a storing means for storing a predetermined threshold for defining an effective range for correction of said electrical main signal by said correcting means,
   wherein said correcting means comprises an error processing means for comparing an index value corresponding to said ratio of said measured values of said plurality of electrical auxiliary signals with said predetermined threshold and for carrying out error processing if said index value departs from said effective range.

5. The multi-angle colorimeter according to claim 1, wherein said main light receiving window includes a plurality of main light receiving windows disposed on said reference plane for receiving lights reflected at different angles from each other from said predetermined measurement point.

* * * * *